United States Patent [19]

Liang

[11] Patent Number: 4,689,152
[45] Date of Patent: Aug. 25, 1987

[54] APPARATUS AND METHOD FOR MULTISTAGE MEMBRANE PHASE SEPARATION

[75] Inventor: Yola Y. Liang, Midland, Mich.

[73] Assignee: The Dow Chemical Company, Midland, Mich.

[21] Appl. No.: 859,178

[22] Filed: May 2, 1986

[51] Int. Cl.⁴ .............................................. B01D 13/00
[52] U.S. Cl. .................................. 210/649; 210/656; 210/336
[58] Field of Search ............... 210/640, 644, 641, 649, 210/655, 656, 321.1, 335, 659, 336

[56] References Cited

U.S. PATENT DOCUMENTS

| | | | |
|---|---|---|---|
| 3,170,867 | 2/1965 | Loeb et al. | 210/655 X |
| 4,218,312 | 8/1980 | Perry | 210/640 |
| 4,350,594 | 9/1982 | Kawai et al. | 210/641 X |
| 4,431,545 | 2/1984 | Pall et al. | 210/641 |

OTHER PUBLICATIONS

Nord et al., Extraction Based on the Flow-Injection Principle; Analytica Chimica Acta, 118 (1980) pp. 285-292.
Moore, W. J., *Physical Chemistry*, 3rd ed., 1964, Prentice Hall, p. 730.
Hwang et al., *Membranes in Separations*, 1984, Krieger Publishing Co., pp. 325-334.
Fossey et al., Simultaneous Monitoring of Both Phases in the Solvent Extraction/Flow Injection Analysis of Dramamine Tablets, 1983, pp. 1882-1885.

*Primary Examiner*—Frank Spear
*Attorney, Agent, or Firm*—Timothy S. Stevens; Burke M. Halldorson

[57] ABSTRACT

The invention relates to an apparatus and process for the separation of at least a portion of one liquid phase from a mixture of immiscible liquid phases using two porous membranes spaced from one another. Each membrane is wetted only by the one liquid phase to be separated. The mixed phases are pressurized on one side of the first membrane. The one phase to be separated passes through the first membrane into the space between the membranes and then through the second membrane to form a finished stream. Any phase that does not ideally wet the first or second membranes theoretically does not pass through the membranes. However, any such phase that nevertheless does pass through the first membrane, due to operational variations or membrane aging effects, is removed from a space between the membranes and does not effectively contaminate the finished stream.

9 Claims, 1 Drawing Figure

APPARATUS AND METHOD FOR MULTISTAGE MEMBRANE PHASE SEPARATION

FIELD OF THE INVENTION

The invention relates to the field of liquid/liquid phase separation using membranes.

BACKGROUND OF THE INVENTION

Immiscible liquid phases can often be separated simply by gravity settling when each phase has a different density. Continuous separation based on this principle is accomplished by a "decanter" as is well known in the art.

Porous membranes have been used for liquid/liquid phase separation, see for example, Nord et al., *Analytica Chimica Acta*, Vol. 118, 1980, pages 285–292. When one phase wets the porous membrane and the other phase does not, then the membrane wetting phase can pass through the pores of the membrane when driven by hydraulic pressure. However, the phase that does not wet the membrane theoretically is not driven through the pores of the membrane under pressure when the pressure is less than the "crucial pressure." The "crucial pressure" is a function of pore diameter (r), the contact angle of the nonwetting phase on the surface of the membrane ($\theta$) of the surface tension ($\tau$) of the nonwetting phase as theoretically described in the following equation (reference, W. J. Moore, *Physical Chemistry*, 1964, Prentice-Hall, p. 730).

"crucial pressure" = $(2\tau \cos \theta / r)$

A liquid phase that wets a membrane has a negative "crutial pressure."

As a practical matter, membrane phase separators suffer problems of "durability" as described by Nord et al., supra, i.e., eventual passage of undesirable mixed phases through the membrane. The membrane phase separation systems of Nord et al. were considered to have durable performance if they worked longer than two hours.

Among the causes of the durability problem with membrane phase separators is a change in the wetting characteristics of the membrane with use. A new hydrophobic membrane (not wetted by water) may absorb water in time or may adsorb onto its surfaces contaminants that lower the "crucial pressure." Additionally, fluctuations in the surface tension of the phases can cause intermittent failures of a membrane phase separator to completely separate one phase from a mixture of phases.

The present inventor was frustrated by the durability problems of prior membrane phase separation systems used in liquid/liquid segmented flow analytical chemistry applications even when the problem was only occasional or intermittent.

Thus, it is an object of this invention to provide a continuous membrane phase separation process effective to separate at least a portion of one phase from a liquid/liquid phase mixture, said separated phase not containing other liquid phases, said process operable for an extended period of time in excess of eight hours.

Essential to the invention is the staged use of porous membranes. It is well known in the art of material processing to use staged nonporous membranes as generally described in *Membranes in Separations*, Hwang and Kammermeyer, 1984, R. E. Krieger Publishing Co., Malabar, Fla., ISBN 0-89874-801-1, pages 325–343. However, little work has been done with staged porous membranes. Pall in U.S. Pat. No. 4,431,545 describes the use of staged porous membranes for a filtration process but without an output port connected to the space between the membranes. Fossey et al. in *Anal. Chem.*, Vol. 55, 1983, pp. 1882–1885 describe a dual porous membrane apparatus for simultaneous monitoring of both phases in the solvent extraction/flow injection analysis of Dramamine ® tablets. However, in the apparatus of Fossey et al. the mixed phase is fed to the space between the membranes and one membrane is hydrophobic while the other membrane is hydrophilic.

BRIEF SUMMARY OF THE INVENTION

The invention relates to a liquid/liquid phase separation apparatus for the effective continuous separation of at least a portion of one liquid phase from a mixture of immiscible liquid phases comprising means for defining a first space, a second space and a third space, wherein: (a) a first porous membrane partitions said first space from said second space, said first porous membrane of a type that is wetted only by said one phase; (b) a second porous membrane partitions said second space from said third space, said second porous membrane of a type that is wetted only by said one phase; (c) an inlet port is in liquid communication with said first space; (d) a first outlet port is in liquid communication with said first space and a first pressure regulation means; (e) a second outlet port is in liquid communication with said second space and a second pressure regulation means; and (f) a third outlet port is in liquid communication with said third space.

The first, second and third spaces of the invention can be defined as channels for liquid communication.

Membranes useful in the invention comprise sheet membranes and tubular membranes and said membranes comprise Teflon ® polyethylene and polypropylene.

The invention also relates to a process for the effective continuous separation of at least a portion of one liquid phase from a mixture of liquid phases comprising the steps of: (a) pressurizing said phases on one side of a first porous membrane wetted by only said one phase to a first hydraulic pressure across said first membrane lower than the crucial pressure of any nonwetted phase/first membrane combination, said first hydraulic pressure effective to drive at least a portion of said one phase through said first membrane; and (b) pressurizing said portion of said one phase that was driven through said first membrane on one side of a second porous membrane wetted by only said one phase to a second hydraulic pressure across said second membrane lower than the crucial pressure of any nonwetted phase/second membrane combination, said second hydraulic pressure effective to drive at least a portion of said one phase through said second membrane, said second membrane effective to prevent any phase that does not wet said first membrane and passes through said first membrane from passing through said second membrane.

The process of the invention is useful, for example, in a liquid/liquid segmented flow injection analysis system and in liquid chromatography systems employing liquid/liquid segmented flow.

DETAILED DESCRIPTION OF THE INVENTION

Figure 1:
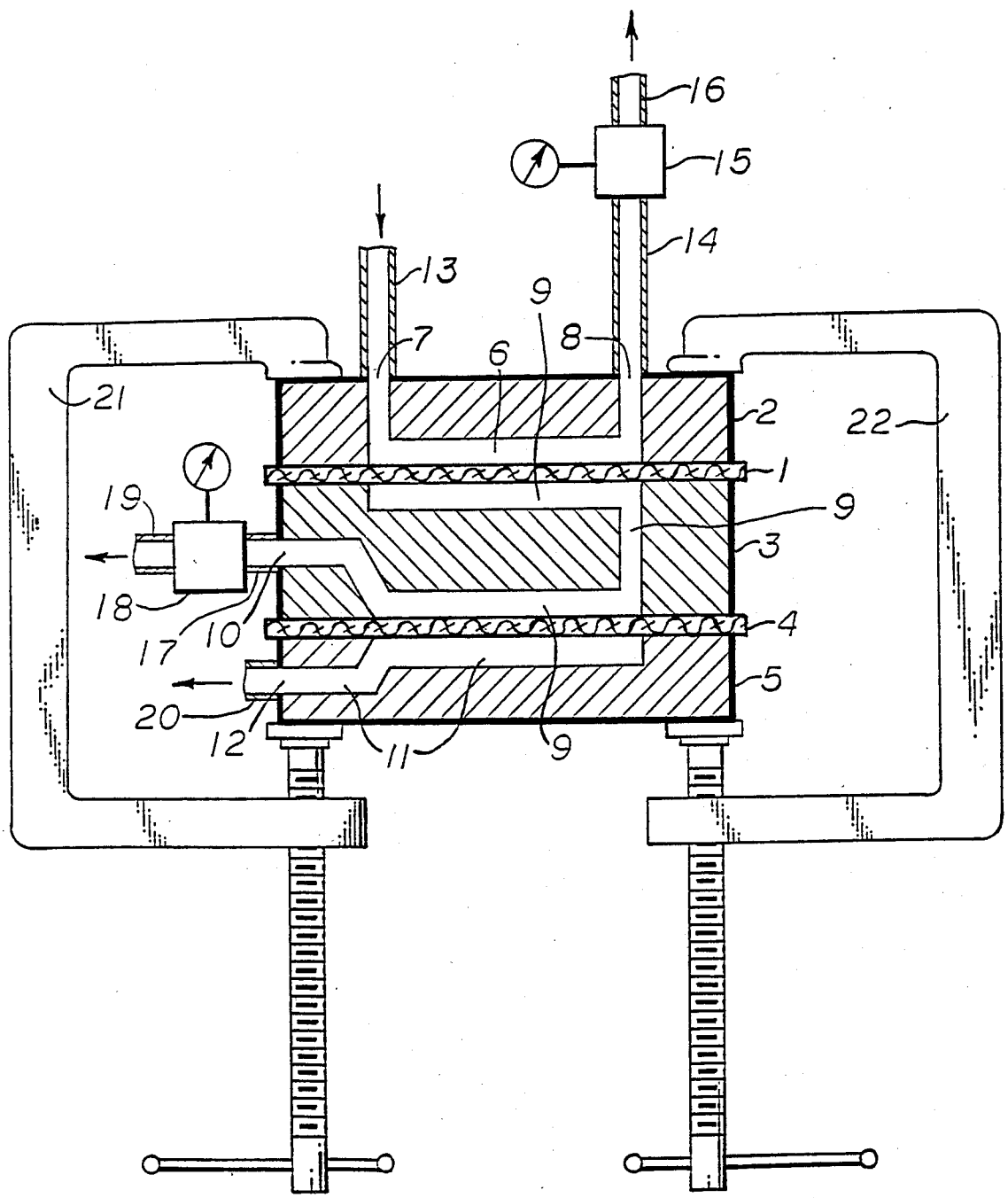
FIG. 1 is a drawing of a typical apparatus of the invention.

Referring to FIG. 1, therein is shown a cross-sectional view of a typical apparatus of the invention. A first porous membrane 1 is sandwiched between an upper plate 2 and a center plate 3. A second porous membrane 4 is sandwiched between the center plate 3 and a lower plate 5. A channel 6 in the plate 2 provides liquid communication between a mixed phase inlet port 7 and a first outlet port 8. The channel 6 is exposed to the membrane 1. A channel 9 in the plate 3 is exposed to the membrane 1, to the membrane 4 and provides liquid communication to a second outlet port 10. A channel 11 in the plate 5 is exposed to the membrane 4 and provides liquid communication to a third outlet port 12. Clamps 21 and 22 compress together the above-described plate and membrane assembly. Alternatively, the above-described plate and membrane assembly can be compressed together by other means such as bolts.

Mixed phases flowing in a tube 13 at a preselected flow rate enter the inlet port 7 and flow in the channel 6 to the first outlet port 8. Mixed phases flow out of the port 8 and into a tube 14, then to a pressure regulation means 15 and then out of the pressure regulation means 15 in a tubing 16. The pressure regulation means 15 maintains a positive hydraulic pressure in the channel 6 higher than in the channel 9 and the pressure differential between the channel 6 and the channel 9 is less than the crucial pressure for the phase that does not wet the membrane 1. A portion of the phase that does wet the membrane 1 flows through membrane 1 from the channel 6 to the channel 9 and then flows in the channel 9 to the second outlet port 10. From the second outlet port 10 said phase flows in a tube 17 to a pressure regulation means 18 and then out of the pressure regulation means 18 in a tubing 19. The membrane 4 is wetted by the same phase that wetted the membrane 1 and the membrane 4 is not wetted by any phase that did not wet the membrane 1. The pressure regulation means 18 maintains a positive hydraulic pressure in the channel 9 higher than in the channel 11 and the pressure differential between the channel 9 and the channel 11 is less than the crucial pressure for the phase that does not wet the membrane 4. A portion of the liquid in the channel 9 flows through the membrane 4 to the channel 11 and then flows to the third outlet port 12. From the third outlet port 12 said liquid flows out in a tube 20. The pressure regulation means 15 and 18 can be valves that throttle flow therethrough to regulate pressure and can simply be a preselected length of tubing of an internal diameter effective to throttle flow therethrough to regulate pressure.

The plates 2, 3 and 5 are preferably made from an inert polymer such as Teflon or polypropylene. The specific pressure regulation set points depend on the specific flow resistance of the membranes (which is a function of the pore size distribution of the membranes, the thickness of the membranes and the number of pores exposed for flow through the membranes) and the input flow rate of the mixed phases. The specific pressure regulation set points are not critical in the invention within the boundaries stated above. However, it is generally desirable to operate at pressures far enough below the crucial pressures (especially for the pressure across the first porous membrane) to allow for some margin of variation in operational parameters.

Although the invention can be operated under conditions where essentially all of the phase that wets the membranes passes through the first porous membrane, it is often desirable to adjust the pressure regulation means 15 and 18 so that the outlet stream at the port 8 still contains a fraction of said phase that wets the membrane 1. This mode of operation minimizes the tendency for the phase that does not wet the first membrane from nevertheless passing through the first membrane. Theoretically, this should not happen if the pressure differential across the first membrane is less than the crucial pressure. However, the crucial pressure referred to here and in the claims is that of a new membrane. As the membranes are used, their actual crucial pressures can change as noted above.

The purpose of the second membrane is to "twice purify" the phase that wets the membranes. The use of the second membrane significantly lengthens the time span before the membranes need to be cleaned or replaced. This is believed to be a result of at least two factors; (a) the second membrane is generally exposed to much less of any phase that does not wet the membranes; and (b) the first membrane acts as an adsorbant for contaminants that can change the crucial pressure characteristics of the porous membrane, said first membrane thus removing said contaminants before they can contaminate the second membrane. Thus, the first membrane's performance can deteriorate so much that a significant amount of a phase that did not wet the new first membrane is exposed to the second membrane, eventually resulting in some mixed phase output from the third outlet port of the invention. At this time the membranes of the invention require cleaning or replacement despite the significantly longer time of operation of the invention relative to the prior use of only one porous membrane in a phase separation device.

The porous membranes useful in the invention can be wetted by water (a hydrophilic membrane) or not wetted by water (a hydrophobic membrane). A preferred hydrophilic membrane is believed to be ordinary high wet strength filter paper such as Whatman No. 2. When hydrophilic membranes are used they should be wetted with water first before being exposed to mixed phases. Generally, the invention is used with hydrophobic membranes. A highly preferred hydrophobic membrane comprises porous Teflon. Porous Teflon membranes were preferred with the prior membrane phase separators due to their durability in excess of two hours, see Nord et al., supra. A specific preferred porous Teflon membrane is available from Control Equipment Corporation, Lowell, Mass., 01851, as part number 8200-0201. A highly preferred porous Teflon membrane, having a pore size of about 1 micron, is available from Fisher Scientific Co., Pittsburgh, Pa., 15219, as Catalog number F10-LP090-25. A preferred porous polypropylene membrane is available from the Celanese Corporation, Box 32414, Charlotte, N.C. 28232, as Celgard 2400 or Celgard 2500.

The invention is particularly useful for phase separation of liquid/liquid segmented flow streams used in application for analytical chemistry. In these segmented flow streams, segments of a liquid phase are interspersed with segments of another immiscible liquid phase in a conduit (usually a tube), see Nord et al., supra. However, the invention is not limited to applications for analytical chemistry and could be beneficially used, for example, in applications for chemical processing, food processing, drug processing or processing biological materials.

FIG. 1 shows the use of sheet-type porous membranes. The invention can also use tubular membranes and the term tubular membranes is meant to include hollow fiber membranes here and in the claims.

EXAMPLES

The following examples are provided as illustrative of the invention.

EXAMPLE 1

This example is a liquid/liquid extraction/flow injection analysis of tetrabutylammonium bromide (TBABr) using the invention. TBABr forms a blue colored product when reacted with bromophenol blue in a dilute aqueous sodium carbonate solution. The colored product can then be extracted with chloroform and the amount of TBABr estimated by photometric analysis of the chloroform extract since unreacted bromophenol blue is essentially not extracted into chloroform. Analytical chemistry systems such as this have been incorporated with flow injection analysis, see Nord et al., supra.

An Altex 110A HPLC pump is used to pump a solution of 800 ppm bromophenol blue and 2 percent sodium carbonate in water at a flow rate of 0.5 ml/min to a 1/16 inch tee using 0.020 inch I.D., 1/16 inch O.D. stainless steel tubing. Another Altex 110A HPLC pump is used to pump chloroform at a flow rate of 0.5 ml/min to the 1/16 inch tee, above, using 0.020 inch I.D., 1/16 inch O.D. stainless steel tubing. Both Altex 110A pumps are equipped with pulse dampeners to provide essentially pulse free flow to the 1/16 inch tee. The 1/16 inch tee is also connected to a Rheodyne No. 7050 injection valve using 0.030 inch I.D., 1/16 inch O.D. Teflon tubing. The injection valve is equiped with a Teflon tubing sample loop of ~50 µl volume. Segmented flow of the aqueous phase/chloroform phase occurs in the tubing between the 1/16 inch tee and the injection valve.

A dual membrane phase separation device generally similar to FIG. 1 is assembled using Teflon plates 2, 3 and 5 wherein the channels exposed to the membranes were each ~40 mm long, ~0.5 mm deep and ~1.2 mm wide with ~1.2 mm bored passageways to the inlet and outlet ports. A 60 cm length of 0.030 inch I.D., 1/16 inch O.D. Teflon tubing is used to conduct the segmented flow stream from the injection valve to the inlet port of the phase separation device. Both membranes in said device are Fischer Scientific porous Teflon membranes Catalog number F10-LP090-25. An Altech Associates (Deerfield, Ill. 60015) Catalog number 8612 flow control needle valve is connected to the first outlet port of the phase separation device as the first pressure regulation means. A 230 cm long coil of 0.030 inch I.D.×1/16 inch O.D. Teflon tubing is connected to the second outlet port of said device as the second pressure regulation means. The third outlet port of said device is connected to a Perkin Elmer Model LC-55 flow through photometric detector (set for detection at 606 nm) using a 30 cm long section of 0.030 inch I.D., 1/16 inch O.D. Teflon tubing. The LC-55 detector is connected to a Hewlett-Packard Model HP3390 recorder-integrator.

The flow control valve, above, is adjusted so that the flow rate through the valve is ~0.5 ml/min, i.e., so that essentially all of the chloroform in the segmented flow stream entering the phase separation device passes through the first membrane. The flow rate of liquid from the second outlet port of said device is ~0.2 ml/min and this stream contains little water phase. The flow rate of liquid from the third outlet port is ~0.3 ml/min and this stream contains essentially no water phase which if present tends to become immobilized on the cell windows of the detector, seriously interfering with the detector.

Six standards of TBABr in water are prepared in the range of from ~58 ppm to ~350 ppm. When each standard is injected, a response peak is seen about 0.7 minutes later. The area of the response peak is proportional to the amount of TBABr injected. When a single standard of ~58 ppm TBABr is injected 9 times, the standard deviation is ±5 ppm. The system is used for 5 days, 8 hours each day and continues to work without interference from water phase in the stream emerging from the third output port of the membrane phase separation device.

This example demonstrates the long term durability of the invention used in a liquid/liquid extraction flow injection analysis system.

EXAMPLE 2

This example is of a liquid/liquid extraction of the effluent from a DuPont Zorbax ODS reverse phase column 6.2 mm I.D.×80 mm long using the invention. An organic compound (0,0-diethyl-O-3,5,6-trichloro-2-pyridyl phosphorothioate) separated on the reverse phase column and emerging in the effluent stream from the column is first detected by an HPLC detector and then extracted into hexane. The hexane extract is then subjected to normal phase HPLC to determine the concentration of the extracted compound.

The phase separation system is identical to that of Example 1, except that; (a) instead of chloroform, hexane is pumped at 0.5 ml/min to the 1/16 inch tee; (b) instead of the bromophenol blue solution, the reverse phase column effluent composed of 82 percent acetonitrile/18 percent water is directed to the 1/16 inch tee at a flow rate of 0.5 ml/min; and (c) the output stream from the third output port of said device is directed to a normal phase HPLC system to determine the above-identified compound.

The first pressure regulation means (the flow control valve) is adjusted so that the output stream from the first output port of said device has a phase ratio of about 50:50. Thus, only a portion of the hexane/acetonitrile phase passes through the first membrane and a portion (about half) passes over the first membrane to the first outlet port. The hexane/acetonitrile stream emerging from the third outlet port contains effectively no aqueous phase, but does contain the extracted organic compound.

A Kratos Model 773 HPLC detector, set to detect at 290 nanometers, is placed between the reverse phase column above and the phase separation system to detect the emergence of the organic compound from the reverse phase column and to predict the emergence of the extracted compound in the hexane/acetonitrile phase emerging from the third outlet port of the invention which is directed to a Rheodyne Model 7125 sample injection valve and through a 2 ml sample loop mounted on the valve. When the extracted compound in the hexane/acetonitrile phase is in the sample injection loop, the injection valve is rotated to inject the contents of the loop onto a 4.6 mm I.D.×250 mm long DuPont Zorbax CN normal phase HPLC column using an eluent of hexane at a flow rate of 1 ml per minute. The organic compound is retained on the normal phase column while the acetonitrile is washed off the column by continuing to elute with hexane for 5 minutes. Then, the eluent through the normal phase column is changed from hexane to 5 percent methylene chloride, 95 percent hexane, at a flow rate of 1 ml per minute, which elutes the organic compound through the column and eventually into the effluent from the column which is directed through another Kratos Model 773 HPLC detector, set to detect at 290 nanometers, which allows quantitation of the organic compound as a chromatographic peak.

The interfacing of the reverse phase HPLC system with the normal phase HPLC system using the invention provides better separation of other organic compounds from the organic compound described above than can be accomplished using either HPLC system alone. This reverse phase/normal phase HPLC system using the invention is used for 5 days, 8 hours each day for determinations of the organic compound and continues to work without the adverse appearance of aqueous phase in the stream emerging from the third output port of the invention. It is important that aqueous phase not be in the hexane/acetonitrile phase because the aqueous phase, if present, will interfere with the chromatographic performance of the normal phase HPLC column.

This example demonstrates the long term durability of the invention used in a liquid/liquid extraction/HPLC system.

What is claimed is:

1. A liquid/liquid phase separation apparatus for the effective continuous separation of at least a portion of one liquid phase from a mixture of immiscible liquid phases comprising means for defining a first space, a second space and a third space, wherein:
   (a) a first porous membrane partitions said first space from said second space, said first porous membrane of a type that is wetted only by said one phase;
   (b) a second porous membrane partitions said second space from said third space, said second porous membrane of a type that is wetted only by said one phase and having pores of about the same diameter as the pores of said first porous membrane;
   (c) an inlet port is in liquid communication with said first space;
   (d) a first outlet port is in liquid communication with said first space and a first pressure regulation means;
   (e) a second outlet port is in liquid communication with said second space and a second pressure regulation means; and
   (f) a third outlet port is in liquid communication with said third space.

2. The apparatus of claim 1 wherein:
   (a) said first space is a channel having said inlet port at one end, said first outlet port at the other end and a central portion exposed to said first membrane;
   (b) said second space is a channel, said channel having four portions in sequence, said sequence being a first portion exposed to said first membrane, a second portion connecting the first portion with a third portion, said third portion exposed to said second membrane and a fourth portion connecting said second outlet port with said third portion; and
   (c) said third space is a channel having two portions in sequence, said sequence being a first portion exposed to said second membrane and a second portion connecting said third outlet port with said first portion of said third space channel.

3. The apparatus of claim 1 or claim 2 wherein one or more of said membranes is a sheet form membrane.

4. The apparatus of claim 1 or claim 2 wherein one or more of said membranes is a tubular membrane.

5. The apparatus of claim 1 or claim 2 wherein said membranes comprise Teflon, polyethylene or polypropylene.

6. A process for the effective continuous separation of at least a portion of one liquid phase from a mixture of liquid phases comprising the steps of:
   (a) pressurizing said phases on one side of a first porous membrane wetted by only said one phase to a first hydraulic pressure across said first membrane lower than the crucial pressure of any nonwetted phase/first membrane combination, said first hydraulic pressure effective to drive at least a portion of said one phase through said first membrane; and
   (b) pressurizing said portion of said one phase that was driven through said first membrane on one side of a second porous membrane wetted by only said one phase to a second hydraulic pressure across said second membrane lower than the crucial pressure of any nonwetted phase/second membrane combination, said second hydraulic pressure effective to drive at least a portion of said one phase through said second membrane, said second membrane effective to prevent any phase that does not wet said second membrane and passes through said first membrane from passing through said second membrane.

7. The process of claim 6 used in a liquid/liquid segmented flow injection analysis system.

8. The process of claim 6 used in a liquid chromatography system employing liquid/liquid segmented flow.

9. The process of claim 6 continuously operable for a time in excess of eight hours.

* * * * *